United States Patent [19]

Shapland

[11] Patent Number: 5,042,497

[45] Date of Patent: Aug. 27, 1991

[54] ARRHYTHMIA PREDICTION AND PREVENTION FOR IMPLANTED DEVICES

[75] Inventor: J. Edward Shapland, Shoreview, Minn.

[73] Assignee: Cardiac Pacemakers, Inc., St. Paul, Minn.

[21] Appl. No.: 472,162

[22] Filed: Jan. 30, 1990

[51] Int. Cl.$^5$ ............................................. A61B 5/04
[52] U.S. Cl. .................................. 128/696; 128/671; 128/419 D; 128/702
[58] Field of Search .......... 128/671, 419 PT, 419 PG, 128/419 P, 419 D, 696, 702

[56] References Cited

U.S. PATENT DOCUMENTS

| | | | |
|---|---|---|---|
| 4,569,350 | 2/1986 | Mumford et al. | 128/419 PT |
| 4,712,556 | 12/1987 | Baker, Jr. | 128/419 PG |
| 4,790,318 | 12/1988 | Elmqvist et al. | 128/419 PG |
| 4,791,936 | 12/1988 | Snell et al. | 128/419 PT |
| 4,819,643 | 4/1989 | Menken | 128/419 PG |
| 4,819,662 | 4/1989 | Heil, Jr. et al. | 128/419 P |
| 4,825,869 | 5/1989 | Sasmor et al. | 128/419 PT |
| 4,892,104 | 1/1990 | Ito et al. | 128/419 PT |
| 4,928,690 | 5/1990 | Heilman et al. | 128/419 D |
| 4,960,129 | 10/1990 | dePaola et al. | 128/695 |

OTHER PUBLICATIONS

Pratt et al., "Analysis of Ambulatory Electrocardiograms in 15 Patients During Spontaneous Ventricular Fibrillation With Special . . . ", Nov. 1983, pp. 789–797, JACC vol. 2 No. 5.
Corr et al., "Mechanisms Controlling Cardiac Autonomic Function and Their Relation to Arrhythmogenesis", The Heart and Cardiovascular System, 1986, pp. 1343–1403.
Martin et al., "Heart Rate Variability and Sudden Death Secondary to Coronary Artery Disease During Ambulatory . . . ", Jul. 1987, pp. 86–89, American Journal of Cardiology vol. 60.
Kleiger et al., "Ambulatory Monitoring-Sudden Death" (Abstract), Mar. 1984, p. 547, JACC vol. 3 No. 2.
Magid et al., "Diminished Heart Rate Variability in Sudden Cardiac Death", undated, p. III-241, Abstracts of the 58th Scientific Sessions, No. 964.

Primary Examiner—Francis Jaworski
Assistant Examiner—George Manuel
Attorney, Agent, or Firm—Fleit, Jacobson, Cohn, Price, Holman & Stern

[57] ABSTRACT

A system for predicting and preventing cardiac arrhythmias for use in combination with an implanted arrhythmia treatment device comprising means for sensing the neural activity of a patient and triggering the implanted arrhythmia treatment device to take preventative and curative actions for an impending arrhythmia upon an elevation of the neural activity. The preventative actions include overdrive pacing of the heart, charging a defibrillator capacitor, activating an alternative cardiac sensing scheme, and applying an anti-arrhythmia drug to the heart of a patient.

29 Claims, 2 Drawing Sheets

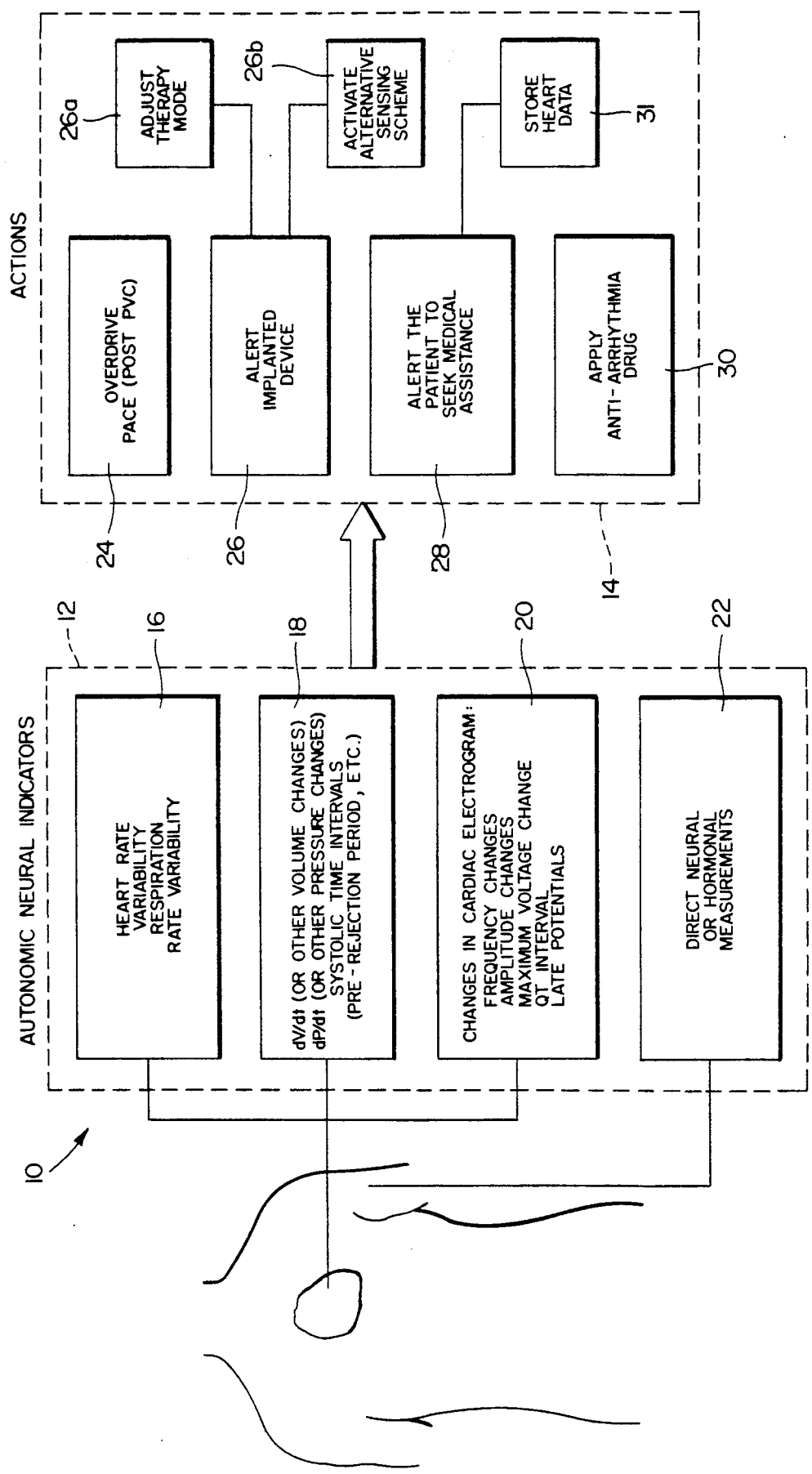

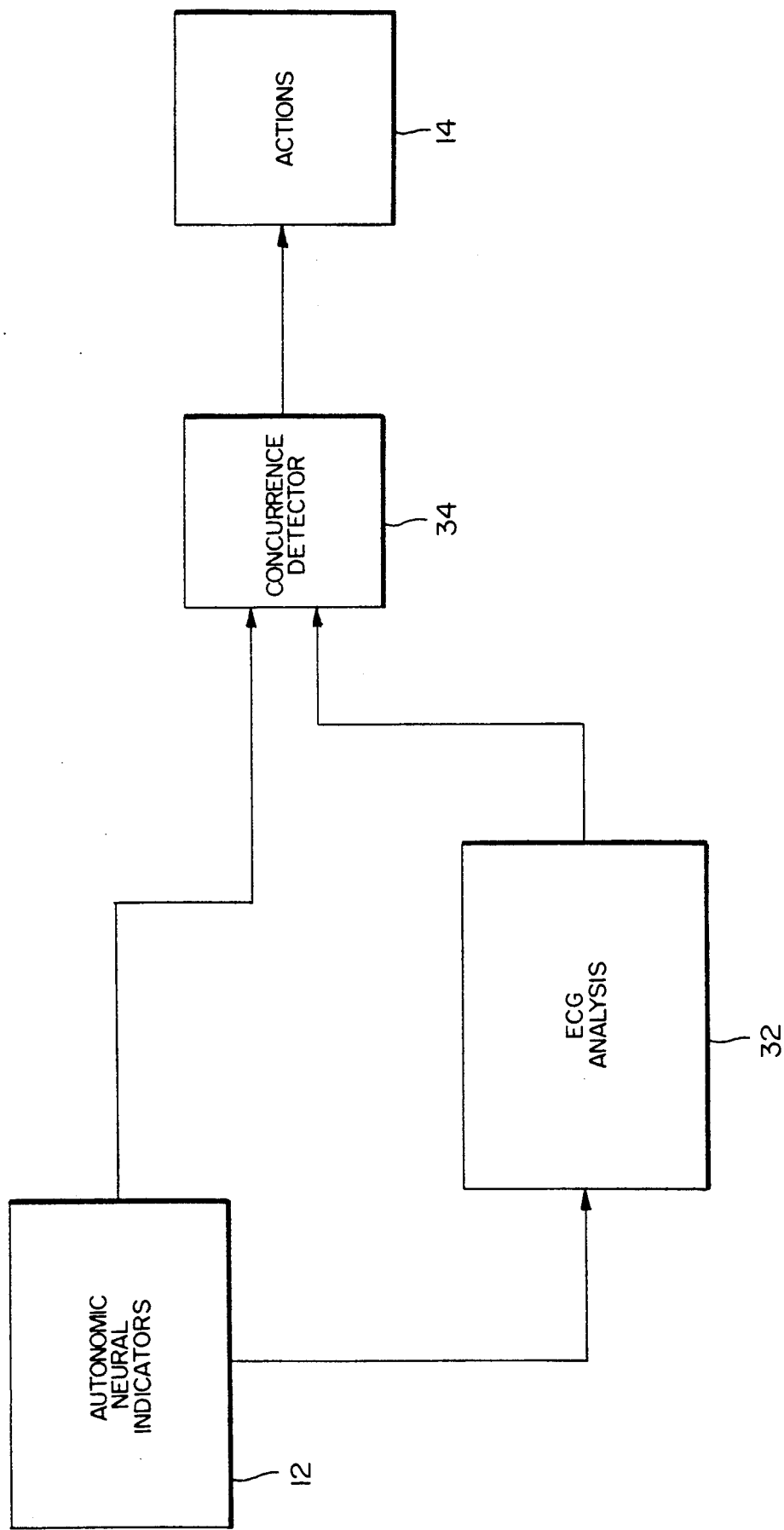

ARRHYTHMIA PREDICTION AND PREVENTION FOR IMPLANTED DEVICES

BACKGROUND OF THE INVENTION

The present invention relates to a system for sensing neural tones and taking steps to prevent or prepare for an impending arrhythmia event.

Presently, conventional arrhythmia conversion devices, including tachyarrhythmia devices, respond to detected arrhythmia events. These devices cannot predict when an event may occur. As such, action is taken by the implantable device only after a life threatening condition occurs. There is no warning of an impending life threatening condition to allow an implantable device to prepare for treating the condition.

An implantable or other device that is capable of determining when a patient has an increased potential for a life threatening arrhythmia event, could react to administer specific therapies to prevent the arrhythmia event, alert the patient or respond to the event more quickly. Specifically, there is evidence that individuals experiencing ventricular arrhythmias also have altered levels of autonomic nervous system activity, elevated sympathetic and/or reduced parasympathetic activity. A device that could monitor autonomic activity, via heart rate variability, respiration rate variability, intracardiac electrogram, or analysis of other physiological parameters, may be able to predict when a patient is at an elevated risk of a ventricular arrhythmia which may present a sudden death situation. The device could then take appropriate preventative measures to prepare for or prevent the arrhythmia event or curative measures to treat the event.

SUMMARY OF THE INVENTION

It is a primary object of the present invention to detect certain physiological conditions for predicting when a patient is at an elevated risk of a sudden death cardiac arrhythmia.

It is another object of the present invention to provide a system for monitoring the neural tone of a patient and taking preventative or curative actions in an implanted device upon the occurrence of changes such as, altered levels of neural tone.

It is a further object of this invention to provide a system for monitoring the autonomic neural tone of a patient, monitoring the ECG at the same time and upon an indication of arrhythmia by both the measured electrical activity of the heart and the autonomic neural tone, taking preventative or curative actions in an implanted device in preparation for an impending cardiac arrhythmia event.

The present invention relates to a system for monitoring the autonomic neural tone of a patient and taking preventative or curative actions in an implanted device upon the occurrence of altered levels of the autonomic neural tone. The autonomic neural tone is detected by several methods including heart rate variability, the derivative of the volume or pressure changes in the heart, systolic time intervals, ventricular electrical parameters, and direct neural activity measurements. The type of actions to be taken in response to altered levels of autonomic neural tone include overdrive pacing of the heart to prevent an impending PVC from leading to ventricular fibrillation, alerting an implanted device to charge a defibrillation capacitor or activate an alternative cardiac sensing scheme, alerting the patient to seek medical assistance, and applying an anti-arrhythmia drug to the heart of the patient. In addition, an altered autonomic neural tone can be used as a first criterion for examining the simultaneously monitored ECG of the heart and taking action in an implanted device upon the concurrence of both an altered autonomic neural tone and the detection of an impending arrhythmia by ECG analysis.

The above and other objects will become more apparent when reference is made to the following description, taken in conjunction with the accompanying drawings.

BRIEF DESCRIPTION OF THE DRAWINGS

FIG. 1 is a block diagram illustrating the arrhythmia prevention/treatment system in accordance with the present invention.

FIG. 2 is a block diagram illustrating the arrhythmia prevention/treatment system in accordance with an alternative embodiment of the present invention.

DETAILED DESCRIPTION OF THE DRAWINGS

Referring first to FIG. 1, the arrhythmia prediction and prevention/treatment system is generally shown at 10. The system 10 includes a plurality of autonomic neural monitoring units as shown in block 12. Block 12 is connected to block 14 which includes a plurality of preventative actions to be taken in response to elevated levels of the sympathetic neural tone.

Block 12 includes four methods for monitoring the autonomic neural tone. The first method, shown in block 16, determines heart rate variability or respiration rate variability. Heart rate variability is determined by measuring the interval between heart beats based on sensing and determining the R-R interval. Respiration variability is likewise determined by measuring the interval between respirations. Variability of both parameters is calculated by examining the beat to beat or breath to breath variation as compared to a previously determined standard. Typically, a decrease in variability indicates an elevated sympathetic tone or reduced parasympathetic tone.

The second method, shown in block 18, determines the autonomic neural influence of the pumping function of the heart. One technique measures the derivative with respect to time of the pressure development during cardiac contraction (systole) or volume change during ventricular ejection. An increase in the derivative of ventricular pressure or volume correlates to an elevated sympathetic neural activity. In addition, this method may include measuring the duration of the systolic intervals. The systolic time interval is the interval beginning with isovolumic contraction of the ventricles and ending with the completion of isovolumic relaxation. A longer systolic time interval typically corresponds to lower sympathetic neural activity. On the other hand, a shorter systolic interval corresponds to an elevated level of sympathetic neural activity.

The third method, illustrated in block 20, is directed to the correlation of the electrical activity of the heart with sympathetic neural tone. Shortening of the Q-T interval indicates an increase in sympathetic neural activity. Other electrical changes, such as for example, the peak derivative of voltage change (dV/dt), QRS frequency changes, amplitude changes, may be appropriate indicators of sympathetic tone. Changes in after potentials and the electrical to mechanical coupling of the heart may also be used as an indicator of autonomic tone and/or pending arrhythmias.

Finally, it is possible to directly measure autonomic neural activity by monitoring a representative portion of the nervous system. This is shown in block 22 and can be accomplished by placing sensing electrodes on or near appropriate nerve trunks. In addition, direct sensor measurement of circulating or tissue substances, such as catecholamines, will provide a measure of sympathetic and/or parasympathetic neural activity.

Regardless of the method employed to monitor the autonomic neural activity, a threshold is provided, particular to the specific method, which must be at least met to trigger actions in block 14. Basically, a baseline threshold is pre-set or otherwise obtained from previous measured values. Then, the real-time measured data is compared to this threshold value to determine the deviation therefrom and the extent of such deviation.

In response to an elevated sympathetic neural tone, one or more preventative or curative actions can be taken as illustrated in block 14. Often, an increase in the sympathetic or decrease in parasympathetic neural tone creates the necessary conditions for a PVC to trigger a tachyarrhythmia. Therefore, one action to prevent the PVC from causing a VT or ventricular fibrillation is to overdrive pace the heart to suppress premature contractions, as shown in block 24. The device could give single or multiple site pacing immediately following the PVC to prevent arrhythmia development. Alternatively, an implanted device could be alerted for preparing for a possible arrhythmia as shown in block 26. Specifically, in block 26a a defibrillator capacitor can be charged so that if defibrillation does occur, the capacitor will be charged and a defibrillation pulse immediately can be delivered to the heart. In addition, other therapy modes can be adjusted based on the autonomic level. Also, in block 26b, an alternative sensing scheme can be triggered in the implanted device for further monitoring the activity of the heart.

Another preventative action may comprise alerting the patient by an alarm to seek further medical assistance as shown in block 28. In addition, another preventative action may comprise the application of a cardiovascular drug such as an anti-arrhythmia drug to the heart to assist in the prevention of a possible arrhythmia, as shown in block 30.

Further, as an additional response, rather than only alerting the patient to seek medical attention, the device could store data for later retrieval by a physician as shown at 31. For example, heart rate variability could be tracked over several weeks, stored in the implanted device, and displayed for the physician at the next physician visit.

FIG. 2 illustrates an alternative embodiment wherein the monitoring of autonomic neural activity is a first criterion which is combined with ECG analysis being performed simultaneously as shown in block 32. In this embodiment, altered levels of autonomic neural activity triggers the implanted device to examine the ECG of the heart already being monitored. Should both the autonomic neural analysis and ECG analysis, such as changes in frequency of the QRS, indicate that an arrhythmia is impending or presently occurring, as detected by the coincidence detector 34, preventative actions are then taken as shown in block 14. In addition, the neural activity can be monitored over a predetermined period of time or a predetermined number of heart beats as a prerequisite for taking a preventative action if an alerting type of neural activity continues over the predetermined period of time or number of heart beats.

By the present invention, the ability to predict and subsequently prevent the actual occurrence of a cardiac arrhythmia is accomplished. In addition, should the steps taken to prevent the arrhythmia fail, alternative curative steps are still taken to successfully treat the heart upon the occurrence of the arrhythmia.

Furthermore, although the primary predictive capability of the present invention is expressed through the sympathetic nervous system, there is evidence that indicates that the parasympathetic activity may also play some role in this type of arrhythmia prediction. Therefore, detection of parasympathetic activity for the purposes described above is considered to be within the scope and spirit of the present invention. Monitoring the overall autonomic neural activity is thus considered within the scope of the present invention.

The above description is intended by way of example only, and is not intended to limit the present invention in any way except as set forth in the following claims:

I claim:

1. A system for predicting and preventing cardiac arrhythmias for use in combination with an implantable arrhythmia treatment device, said system comprising:
   means for monitoring the neural activity of a patient to predict an impending arrhythmia;
   means for taking actions in said implantable arrhythmia treatment device prior to an initial irregular beat of said impending arrhythmia to prevent the initial irregular beat or prepare for said arrhythmia upon said means for monitoring detecting a predetermined change in said neural activity.

2. The system of claim 1, wherein the neural activity being monitored is sympathetic or parasympathetic neural activity.

3. The system of claim 1, wherein said means for monitoring comprises means for determining the heart rate variability based upon the interval between consecutive heart beats.

4. The system of claim 1, wherein said means for monitoring comprises means for determining the respiration rate variability based upon the interval between consecutive breaths.

5. The system of claim 1, wherein said means for monitoring comprises means for measuring the systolic time interval of the heart.

6. The system of claim 1, wherein said means for taking actions comprises means for overdrive pacing the heart.

7. The system of claim 1, wherein said means for taking actions charges a defibrillation capacitor in said implanted device in preparation for delivering a defibrillation pulse to the patient.

8. The system of claim 1, wherein said means for taking actions comprises means for adjusting a particular mode of therapy.

9. The system of claim 1, wherein said means for taking actions comprises means for activating a cardiac sensing scheme in said implanted arrhythmia treatment device.

10. The system of claim 1, wherein said means for taking actions comprises means for alerting a patient in which the implantable arrhythmia treatment device is implanted of said impending arrhythmia by said alarm.

11. The system of claim 1, wherein said means for taking actions comprises means for applying a cardiovascular drug to the heat of the patient.

12. The system of claim 1, wherein said means for taking actions comprises means for storing data relating to heart function for later review by a physician.

13. A system for predicting and preventing cardiac arrhythmias for use in combination with an implantable arrhythmia treatment device, said system comprising:
   means for monitoring the sympathetic neural activity of a patient to predict an impending arrhythmia;
   means for monitoring the ECG of the heart of the patient;
   means for detecting the concurrence of both a change in the sympathetic neural activity and an abnormal characteristic of said ECG, and generating a concurrence output signal;
   means for taking actions in said implantable arrhythmia treatment device prior to an initial irregular beat of said impending arrhythmia to prevent the initial irregular beat or prepare for said arrhythmia upon the generation of said concurrence output signal.

14. The system of claim 13, wherein said means for monitoring the autonomic neural activity comprises means for determining the heart rate variability based upon the interval between consecutive heart beats.

15. The system of claim 13, wherein said means for monitoring the autonomic neural activity comprises means for determining the respiration rate variability based upon the interval between consecutive breaths.

16. The system of claim 13, wherein said means for monitoring the autonomic neural activity comprises means for measuring the systolic time interval of the heart.

17. The system of claim 13, wherein said means for taking actions comprises means for overdrive pacing the heart.

18. The system of claim 13, wherein said means for taking actions charges a defibrillation capacitor in said implanted device in preparation for delivering a defibrillation pulse to the patient.

19. The system of claim 13, wherein said means for taking actions comprises means for choosing a particular mode of therapy for preventing the onset of the arrhythmia.

20. The system of claim 13, wherein said means for taking actions comprises means for activating a cardiac sensing scheme in said implanted arrhythmia treatment device.

21. A method for predicting and preventing cardiac arrhythmias comprising the steps of:
   sensing the neural activity of the heart of a patient to predict an impending arrhythmia;
   triggering an implantable arrhythmia treatment device prior to an initial irregular beat of said impending arrhythmia to take actions to prevent the initial irregular beat or prepare for said arrhythmia upon an elevation of the sympathetic neural or reduction in parasympathetic activity.

22. The method of claim 21, wherein said step of sensing senses the sympathetic neural activity of the heart of the patient.

23. The method of claim 21, wherein said step of triggering an implanted arrhythmia treatment device comprises overdrive pacing of the heart.

24. The method of claim 21, wherein said step of triggering an implanted arrhythmia treatment device comprises charging a defibrillation capacitor in preparation for delivering a defibrillation pulse.

25. The method of claim 21, wherein said step of triggering an implanted arrhythmia treatment device comprises activating an alternative cardiac sensing scheme.

26. The method of claim 21, wherein said step of triggering an implanted arrhythmia device comprises the application of a cardiovascular drug.

27. The method of claim 26, wherein said step of triggering an implanted arrhythmia treatment device comprises the application of an anti-arrhythmia drug to the heart of the patient.

28. A method for predicting and preventing cardiac arrhythmias comprising the steps of:
   sensing the neural activity of the heart of a patient to predict an impending arrhythmia;
   sensing the ECG of the heart of the patient;
   triggering an implantable arrhythmia treatment device prior to an initial irregular beat of said impending arrhythmia to take actions to prevent the initial irregular beat or prepare for said arrhythmia upon the concurrence of a change in the neural activity and an abnormal condition of the ECG.

29. The method of claim 26, wherein said step of sensing senses the autonomic neural activity of the heart of the patient.

* * * * *